US006589179B2

(12) United States Patent
Criton et al.

(10) Patent No.: US 6,589,179 B2
(45) Date of Patent: Jul. 8, 2003

(54) THREE-DIMENSIONAL DOPPLER ULTRASONIC IMAGING SYSTEM AND METHOD

(75) Inventors: Aline Criton, Seattle, WA (US); Helen Routh, Briarcliff Manor, NY (US)

(73) Assignee: Koninklijke Philips Electronics NV, Eindhoven (NL)

( * ) Notice: Subject to any disclaimer, the term of this patent is extended or adjusted under 35 U.S.C. 154(b) by 0 days.

(21) Appl. No.: 09/997,229

(22) Filed: Nov. 27, 2001

(65) Prior Publication Data

US 2003/0100832 A1 May 29, 2003

(51) Int. Cl.[7] .................................................. A61B 8/02
(52) U.S. Cl. ........................ 600/454; 600/441; 600/455; 600/456; 600/459; 600/465; 128/916
(58) Field of Search ................................ 600/437–472; 128/916

(56) References Cited

U.S. PATENT DOCUMENTS

| | | | | |
|---|---|---|---|---|
| 4,068,207 A | * | 1/1978 | Andermo et al. ............ 342/105 |
| 4,694,434 A | | 9/1987 | von Ramm et al. ............. 367/7 |
| 4,915,115 A | * | 4/1990 | Sasaki et al. ................ 600/441 |
| 5,127,409 A | * | 7/1992 | Daigle ........................ 600/443 |
| 5,522,393 A | | 6/1996 | Phillips et al. ......... 128/661.09 |
| 5,797,845 A | * | 8/1998 | Barabash et al. ............ 600/443 |
| 6,066,096 A | | 5/2000 | Smith et al. ................. 600/439 |
| 6,241,675 B1 | | 6/2001 | Smith et al. ................. 600/443 |
| 6,276,211 B1 | * | 8/2001 | Smith .......................... 73/626 |
| 6,293,914 B1 | * | 9/2001 | Sumanaweera et al. ...... 600/447 |
| 6,390,981 B1 | * | 5/2002 | Jago ........................... 600/443 |
| 6,419,633 B1 | * | 7/2002 | Robinson et al. ........... 600/443 |
| 6,464,637 B1 | * | 10/2002 | Criton et al. ................ 600/441 |

* cited by examiner

Primary Examiner—Marvin M. Lateef
Assistant Examiner—William C. Jung
(74) Attorney, Agent, or Firm—Dorsey & Whitney LLP

(57) ABSTRACT

An ultrasonic imaging system uses a specially configured scanhead to provide ultrasound return signals that are processed by an imaging unit to generate a three-dimensional Doppler ultrasound image. One embodiment of the scanhead includes a first pair of apertures aligned along a first axis, and a second pair of apertures aligned along a second axis that is perpendicular to the first axis. All of the apertures lie in a common plane. Respective signals from the apertures along each axis are processed to generate two-dimensional Doppler motion vectors. The resulting pairs of two-dimensional Doppler motion vectors are then processed to generate three-dimensional Doppler motion vectors that are used to generate a three-dimensional Doppler image. In another embodiment, three co-planar apertures are arranged equidistantly from each other about a common center, and the three-dimensional Doppler image is generated from respective signals from the apertures.

30 Claims, 6 Drawing Sheets

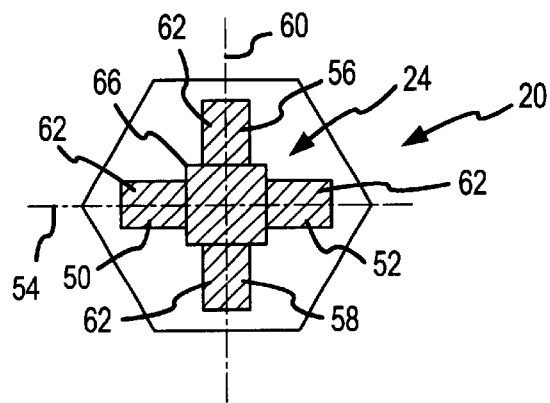
FIG.2
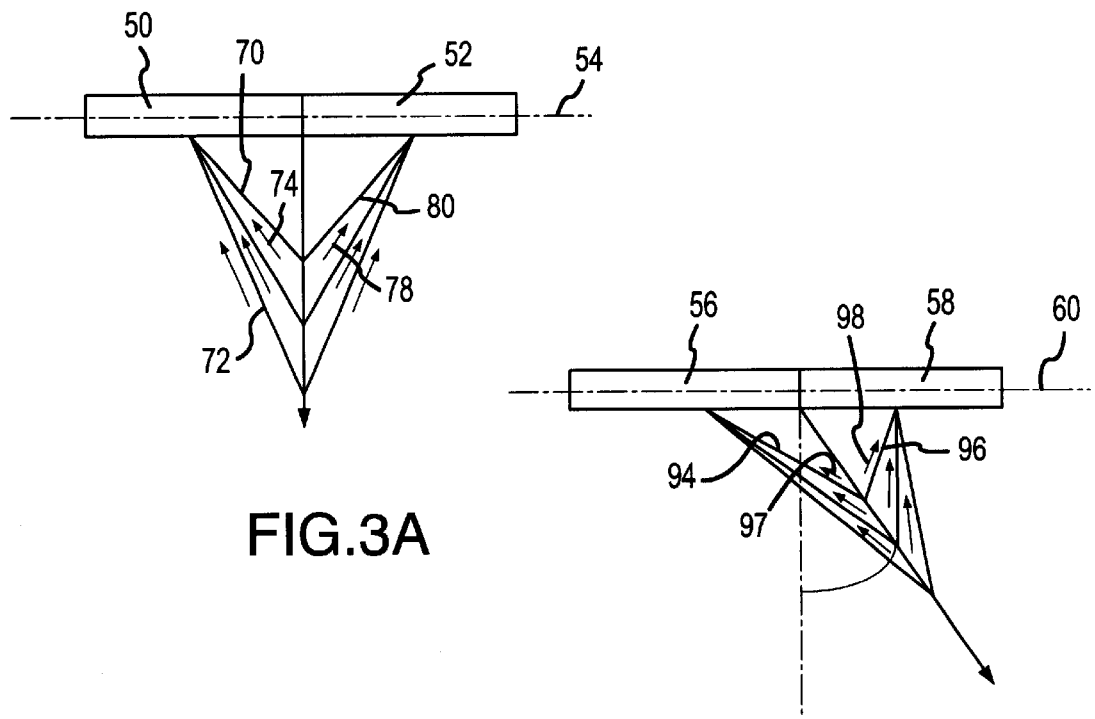
FIG.3A
FIG.3B

THREE-DIMENSIONAL DOPPLER ULTRASONIC IMAGING SYSTEM AND METHOD

TECHNICAL FIELD

This invention relates to ultrasonic diagnostic imaging systems and, in particular, to a method and apparatus for obtaining three-dimensional ultrasonic Doppler images of moving sound reflectors in blood and tissues.

BACKGROUND OF THE INVENTION

A variety of ultrasound imaging modalities have been developed to suit a variety of specific applications. For example, Doppler imaging has been developed to allow the imaging of moving ultrasound reflectors. Doppler ultrasound imaging systems detect a Doppler shift in the frequency of a transmitted signal reflected from ultrasound reflectors, and display returns only from such reflectors. The magnitude of the Doppler shift corresponds to the velocity of the ultrasound reflectors, and the polarity of the Doppler shift corresponds to the direction of movement. Conventional Doppler images are thus able to provide an indication of both blood flow velocity and blood flow direction, thereby allowing arterial blood flow to be differentiated from venous blood flow. Doppler imaging can also be used to visualize the movement of tissues, such as heart wall movement.

Although Doppler imaging provides a great deal of clinically useful information, Doppler imaging is not without its problems and limitations. The magnitude of the Doppler shift corresponds to the projection of the velocity of the blood flow on the ultrasound beam. The Doppler shift from blood flowing at an angle to the axis of the ultrasound beam corresponds to the product of the blood flow velocity and the cosine of the angle between the direction blood flow direction and the axis of the beam. Therefore, the velocity of blood flow can be accurately determined and portrayed in an ultrasound Doppler image only if the angle between the blood flow and the axis of the ultrasound beam is known. Yet it can be difficult to make this determination.

Even if the angle between the axis of the ultrasound beam and an artery or vein is known, it can still be difficult or impossible to accurately determine the velocity of blood flowing through the blood vessel because the flow of blood through a vessel is not always aligned with the axis of the vessel. Blood can flow through a blood vessel in a helical manner. Furthermore, the flow of blood in a blood vessel becomes even more irregular in the presence of bends, bifurcations or obstructions in the vessel. Thus, a single cosine correction angle cannot be used to accurately correct signals indicative of the velocity of moving reflectors in an artery or vein.

In conventional Doppler imaging systems, a two-dimensional Doppler image is obtained by using an ultrasound transducer having a linear, one-dimensional array of transducer elements. Signals applied to or received from the array are combined to form a beam that is steered by phase-shifting the signals to sample locations in a two-dimensional plane. If each sample location in the two-dimensional plane is interrogated from two different apertures, i.e., by two different beams emanating from different locations, the absolute mean velocity of flow at that sample location can be determined in two dimensions. However, such systems are incapable of accurately portraying the true flow velocity because the true velocity may have a component that is perpendicular to the two-dimensional plane.

One approach to determining blood flow in three dimensions is disclosed in U.S. Pat. No. 5,522,393 to Philips et al., which discloses a system using a transducer having a non-planar phased array that interrogates each sample volume using three independently steered beams. Although the two-dimensional phased arrays taught by the Philips et al. patent are capable of accurately determining the velocity of blood flow in three dimensions, the structure of the transducers disclosed in the Philips et al. patent make them difficult to use. In particular, because the faces of the arrays are curved, it can be difficult to maintain good acoustic contact with the surface of tissues to be imaged unless the curvature of the surface is substantially the same as the curvature of the face of the array. However, the curvature of the array face will not generally match the curvature of the surface of tissues to be imaged. The approach described in the Philips et al. patent thus has a limited range of applications. Furthermore, the large number of elements in the array each located in a different three-dimensional position produce respective signals that can be combined only with a great deal of computational complexity.

There is therefore a need for a system and method for providing a three-dimensional Doppler image using an ultrasound transducer that can be used with relative ease and that produces signals that can be combined to create the image with relatively little computational complexity. Furthermore such a system should be capable of imaging both blood flow and tissue motion, in order to determine the true velocity of both heart and vessel wall motion. Delineation of the direction of motion will both make the diagnosis easier and allow better understanding of the source of the motion abnormality.

SUMMARY OF THE INVENTION

An ultrasonic imaging system for generating a three-dimensional Doppler image includes a scanhead and an imaging unit. The scanhead includes a transmit aperture, and at least three receive apertures arranged in a common plane. The imaging unit includes a beamformer coupled to the receive apertures. The beamformer combines signals from several transducer elements in each of the receive apertures to generate signals indicative of ultrasound Doppler returns from a selected volume adjacent the receive aperture. Respective Doppler processors for the receive apertures generate respective magnitude signals indicative of the Doppler flow magnitude of moving ultrasound reflectors in the selected volume and a direction signal indicative of the direction of the moving ultrasound reflectors in the selected volume. A velocity estimator is coupled to receive the magnitude and direction signals from each of the Doppler processors. The velocity estimator generates a magnitude signal indicative of the magnitude of a three-dimensional flow vector corresponding to the magnitude signals from the Doppler processors and a flow angle signal indicative of the direction of the three-dimensional flow vector corresponding to the direction signals from the Doppler processors. The imaging system also includes a display processor coupled to receive the magnitude signal and the angle signal from the velocity estimator. The display processor converts the magnitude and angle signals to display signals having a predetermined display format.

The transmit aperture is preferably positioned symmetrically between the receive apertures and in the common plane of the receive apertures. In one aspect of the invention, the scanhead may include a first pair of receive apertures positioned in the common plane along a first axis, and a second pair of receive apertures positioned in the common plane along a second axis that is perpendicular to and intersects the first axis. In this configuration, the transmit aperture may be positioned in the common plane at the intersection of the first and second axes. In another aspect of the invention, the scanhead may include a plurality of receive apertures equally spaced from a center point of the scanhead and circumferentially spaced from each other. The receive apertures may have a hexagonal shape, and the transmit aperture may be centered at the center point between the receive apertures.

BRIEF DESCRIPTION OF THE DRAWINGS

FIG. 2 is a plan view of a transducer face according to one embodiment of a scanhead that is may be used in the imaging system of FIG. 1.

FIGS. 3A and 3B are schematic views and vector diagrams showing the two orthogonal planes in which blood flow is measured using the scanhead of FIG. 2.

DETAILED DESCRIPTION OF THE INVENTION

Figure 1:
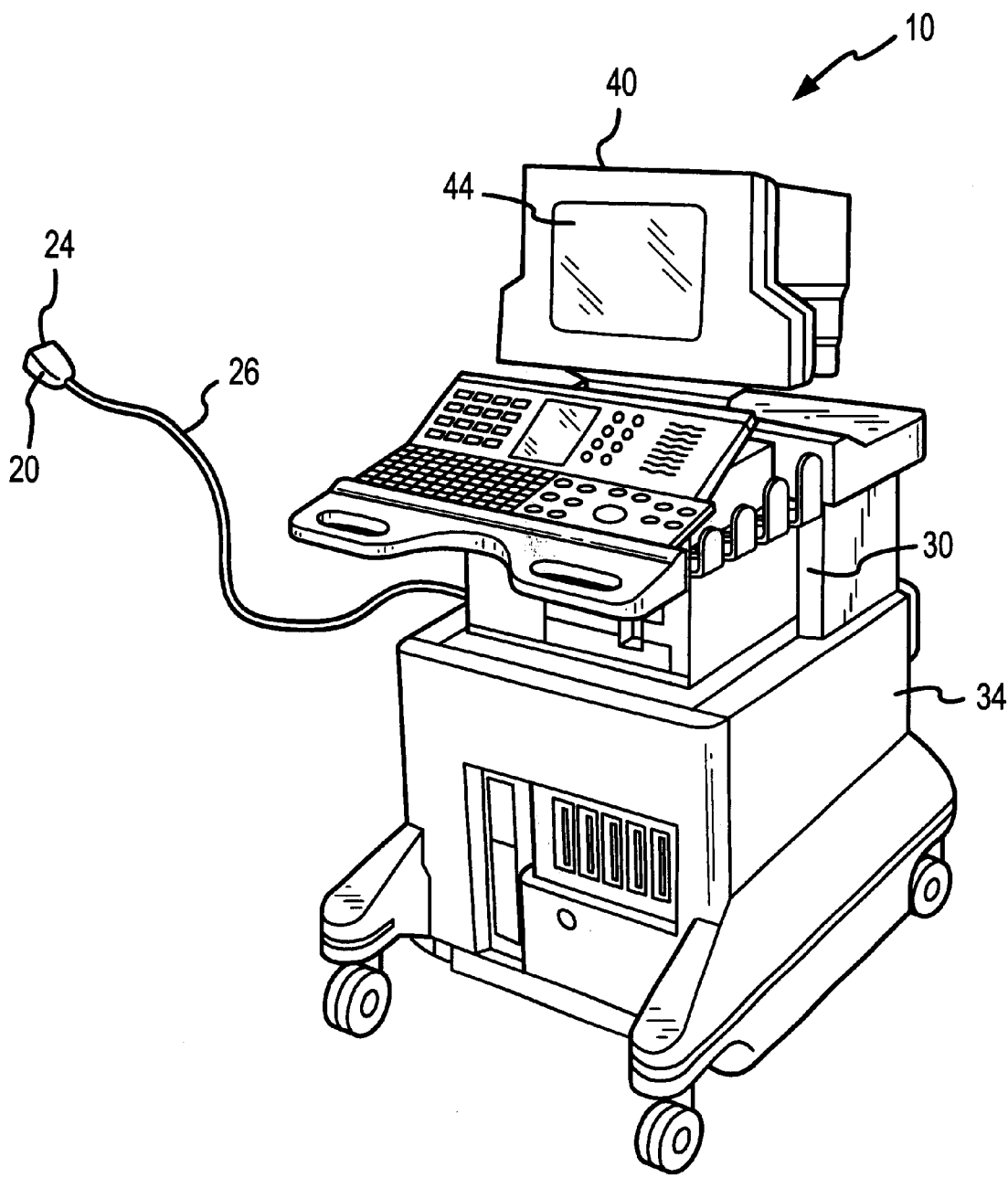
FIG. 1 is an isometric view of one embodiment of a three-dimensional Doppler ultrasound imaging system in accordance with the present invention.

One embodiment of a system 10 for producing a Doppler three-dimensional image is shown in FIG. 1. The ultrasound imaging system 10 includes a scanhead 20 having a transducer face 24 that will be described in greater detail below. Electric signals are coupled between the scanhead 20 and an imaging unit 30 through a cable 26. The imaging unit 30 is shown mounted on a cart 34. A display monitor 40 having a viewing screen 44 is placed on an upper surface of the imaging unit 30.

The transducer face 24 of the scanhead 20 is shown in greater detail in FIG. 2. The face 24 is planar, and it has a first pair of receive apertures 50, 52 extending along a first axis 54, and a second pair of receive apertures 56, 58 extending along a second axis 60 that is perpendicular to the first axis 54. Each receive aperture 50–58 is formed by a plurality of transducer elements 62 generating respective electrical signals responsive to received ultrasound returns. The phasing of the signals from the transducer elements 62 may be adjusted to effectively steer and focus the received ultrasound returns to various directions and depths. A transmit aperture 66 is located at the intersection of the two axes 54, 60. Since the face 24 of the scanhead 20 is planar, it can maintain contact with the surface of tissues to be imaged (not shown) with substantially the same ease that a conventional one-dimensional transducer array (not shown) can maintain contact with the surface of tissues to be imaged. Furthermore, since only four apertures 50, 52, 56, 58 are used to generate signals from ultrasound returns, the signals can be combined to form signals indicative of a three-dimensional flow vector with relatively little computational complexity.

Figure 4A:
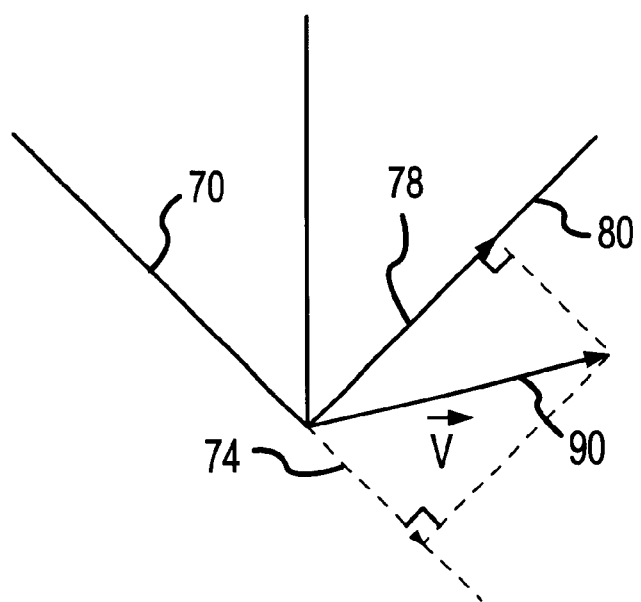
FIGS. 4A and 4B are vector diagrams illustrating the manner in which the Doppler flow vectors shown in FIGS. 3A and 3B, respectively, are resolved into composite vectors that may have two orthogonal components.

The manner in which the scanhead 20 shown in FIG. 2 can determine flow vectors in three dimensions will now be explained with reference to FIGS. 3A and 3B. After the transmit aperture 66 directs ultrasound to tissues adjacent the array face 24, each of the receive apertures 50, 52 detects reflected ultrasound signals. Based on the time at which each portion of the ultrasound signal is received by the transducer elements 62 in each aperture 50, 52, the distance and angle of a sample volume relative to the center of each receive aperture 50, 52 can be determined. Each aperture 50, 52 determines the magnitude of a Doppler flow vector from the sample volume based on the frequencies of the ultrasound returns from the sample volume. For example, with reference to FIG. 3A, the receive aperture 50 is first steered and focused to receive ultrasound returns along a beam 70, and subsequently steered and focused to receive ultrasound returns along a beam 72. With reference to the Doppler shift of the ultrasound returns received along the beam 70, a flow vector 74 having a magnitude corresponding to the projection of the speed of the ultrasound reflectors along the beam 70 can be determined. Similarly, a vector 78 having a magnitude corresponding to the projection of the speed of the ultrasound reflectors along a beam 80 can be determined. Based on these two projected vectors 74, 78, a composite two-dimensional flow vector can be determined by conventional means. For example, as shown in FIG. 4A, the projected flow vector 74 combined with the projected flow vector 78 results in a composite two-dimensional flow vector 90. The sole component of the vector 90 is in a plane that is perpendicular to the transducer face 24 and containing the axis 54 (FIG. 3A). Any velocity component in a direction perpendicular to this plane cannot be detected by the receive apertures 50, 52. The receive apertures 50, 52 are thus only capable of generating a two-dimensional Doppler image.

Figure 4B:
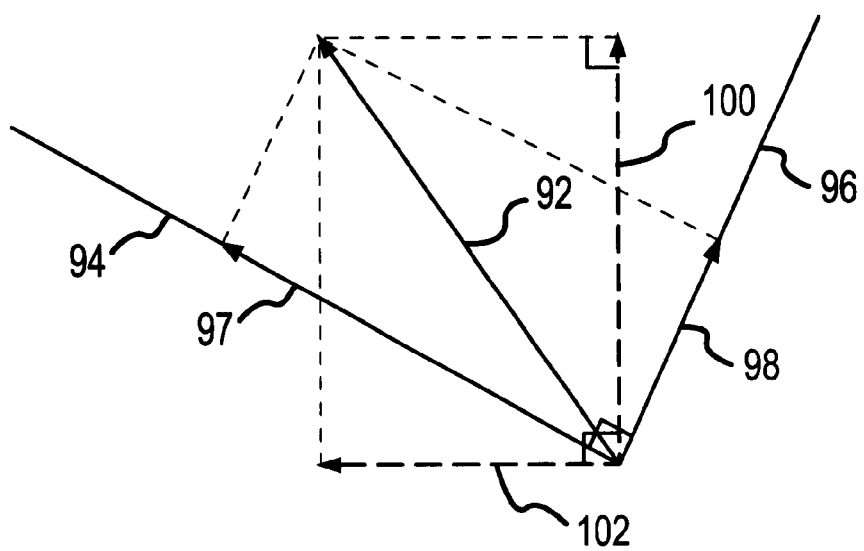

As shown in FIG. 3B, ultrasound returns are received by the receive apertures 56, 58 in the same manner that the receive apertures 50, 52 receive ultrasound returns. In the example of FIG. 3B, the ultrasound returns received by the receive apertures 56 and 58 are "off-axis", i.e., steered to one side. With reference to the Doppler shift of the ultrasound returns received along the beam 94 a flow vector 97 having a magnitude corresponding to the projection of the speed of the ultrasound reflectors along the beam 94 can be determined. Similarly, a vector 98 having a magnitude corresponding to the projection of the speed of the ultrasound reflectors along a beam 96 can be determined. Based on these two projected vectors 97, 98, a composite two-dimensional flow vector we can be determined by conventional means. The composite flow vector 92 along the beam has a first component 100 that is perpendicular to the axis 60 (FIG. 3B) and a second component 102 that is parallel to the axis 60, as shown in FIG. 4B. The composite vector 92 lies in a plane that contains the axis 60 and is perpendicular to the face 24 of the scanhead 20. The vector components 100, 102 also lie in this plane. Any velocity component not in this plane cannot be detected by the receive apertures 56, 58. The receive apertures 56, 58 are thus only capable of generating a two-dimensional Doppler image. The two-dimensional Doppler image is in a plane that is perpendicular to the plane in which a two-dimensional Doppler image can be generated by the receive apertures 50, 52 (FIG. 3A). It will be appreciated that the ultrasound beams can be steered in any direction relative to the scanhead face 24 and apertures 50, 52, 56, 58 and that the directions shown in FIGS. 3A and 3B are examples of only two planar directions which may be employed.

Figure 5:
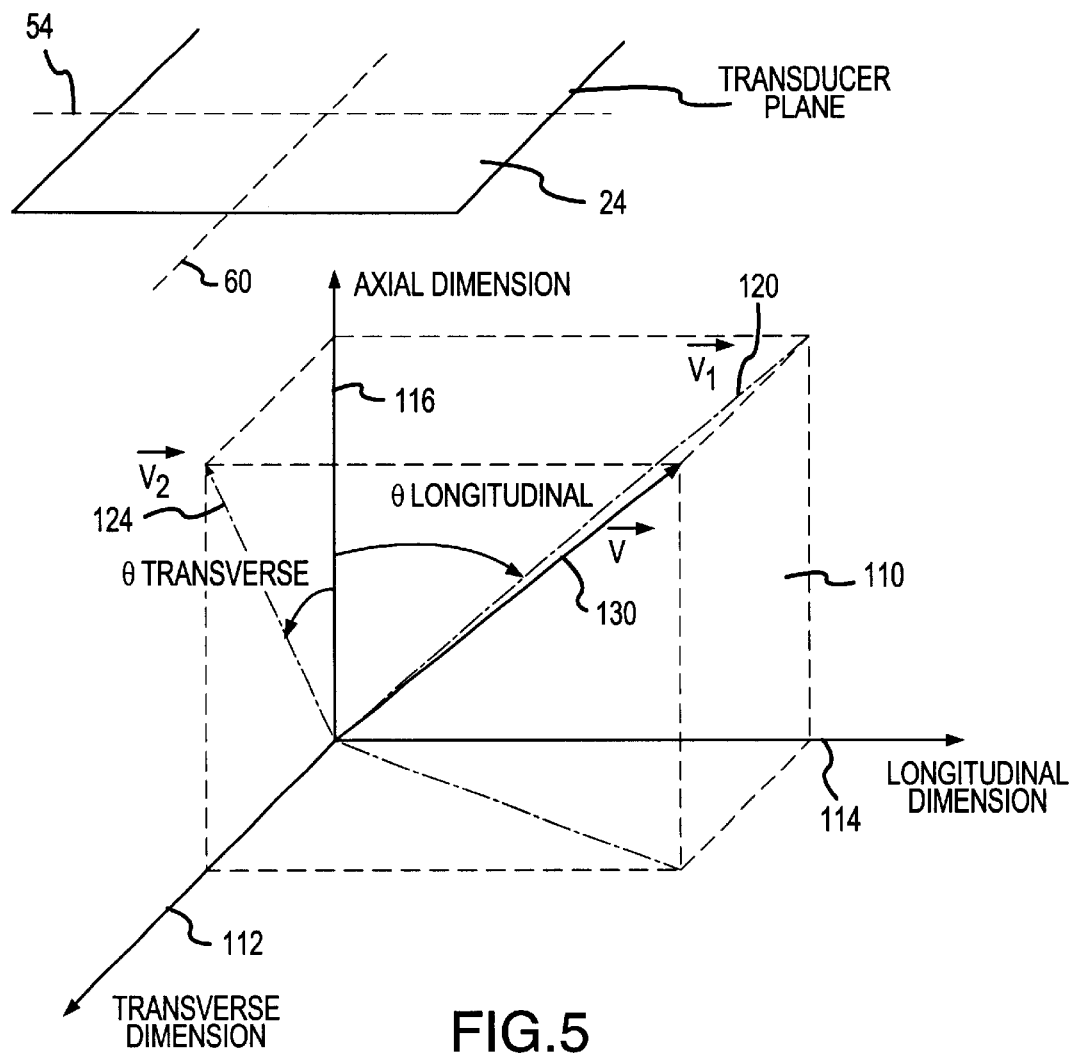
FIG. 5 is a vector diagram illustrating the manner in which the composite vectors shown in FIGS. 4A and 4B, respectively, are resolved into a three-dimensional composite vector that may have three orthogonal components.

The manner in which ultrasound returns from the four receive apertures 50, 52, 56, 58 can be used to provide a three-dimensional Doppler vector will now be explained with reference to FIG. 5. FIG. 5 shows the planar face 24 of the scanhead 20 and the axes 54, 60 described above with reference to FIGS. 2–4. A volume 110 is defined by a three-dimensional Cartesian coordinate system having a transverse dimension 112, a longitudinal dimension 114, and an axial dimension 116. The axial dimension 116 and the longitudinal dimension 114 define a plane that includes the axis 54 and is perpendicular to the face 24 of the scanhead 20. As explained above, the receive apertures 50, 52 (FIGS. 2 and 3A) are capable of detecting Doppler flow vectors to create a composite two-dimensional flow vector in this plane. As also explained above with reference to FIG. 4B, this composite two-dimensional flow vector can be divided into two vector components, one extending in the longitudinal dimension 114 and one extending in the axial dimension 116. This composite two-dimensional flow vector may also be defined in a polar coordinate system by a two-dimensional flow vector 120 having a magnitude $V_1$ and an angle $\theta_{LONGITUDINAL}$ measured from the axial direction. Similarly, the axial dimension 116 and the transverse dimension 112 define a plane that includes the axis 60 and is perpendicular to the face 24 of the scanhead 20. As also explained above, the receive apertures 56, 58 (FIGS. 2 and 3B) are capable of detecting Doppler flow vectors to create a composite two-dimensional flow vector in this plane. As also explained above with reference to FIG. 4A, this composite two-dimensional flow vector can be divided into two vector components, one extending in the transverse dimension 112 and one extending in the axial direction 116. This composite flow vector may also be defined in a polar coordinate system by a two-dimensional flow vector 124 having a magnitude $V_2$ and an angle $\theta_{TRANSVERSE}$ measured from the axial direction 116. The two-dimensional flow vectors 120, 124 may be further combined to create a three-dimensional flow vector 130 that may have components extending in the transverse direction 112, the longitudinal direction 114, and the axial direction 116. This flow vector 130 is a true three-dimensional vector. Individual three-dimensional flow vectors may be obtained in this manner for a large number of sample volumes in the volume 110 being imaged. The true velocity of blood flowing through a vessel can therefore be determined and imaged even though the flow may be helical or in some other even more irregular pattern.

Using the techniques described above, an imaging system of the present invention can be used to provide a three-dimensional image of moving tissues, such as the movement of the heart wall. However, in being used for these applications, the system needs to be modified to selectively respond to lower Doppler frequencies when imaging tissues as compared to the Doppler frequency of interest when imaging blood flow. The likely range of angles of motion will also usually be different to those seen with flow.

Figure 6:
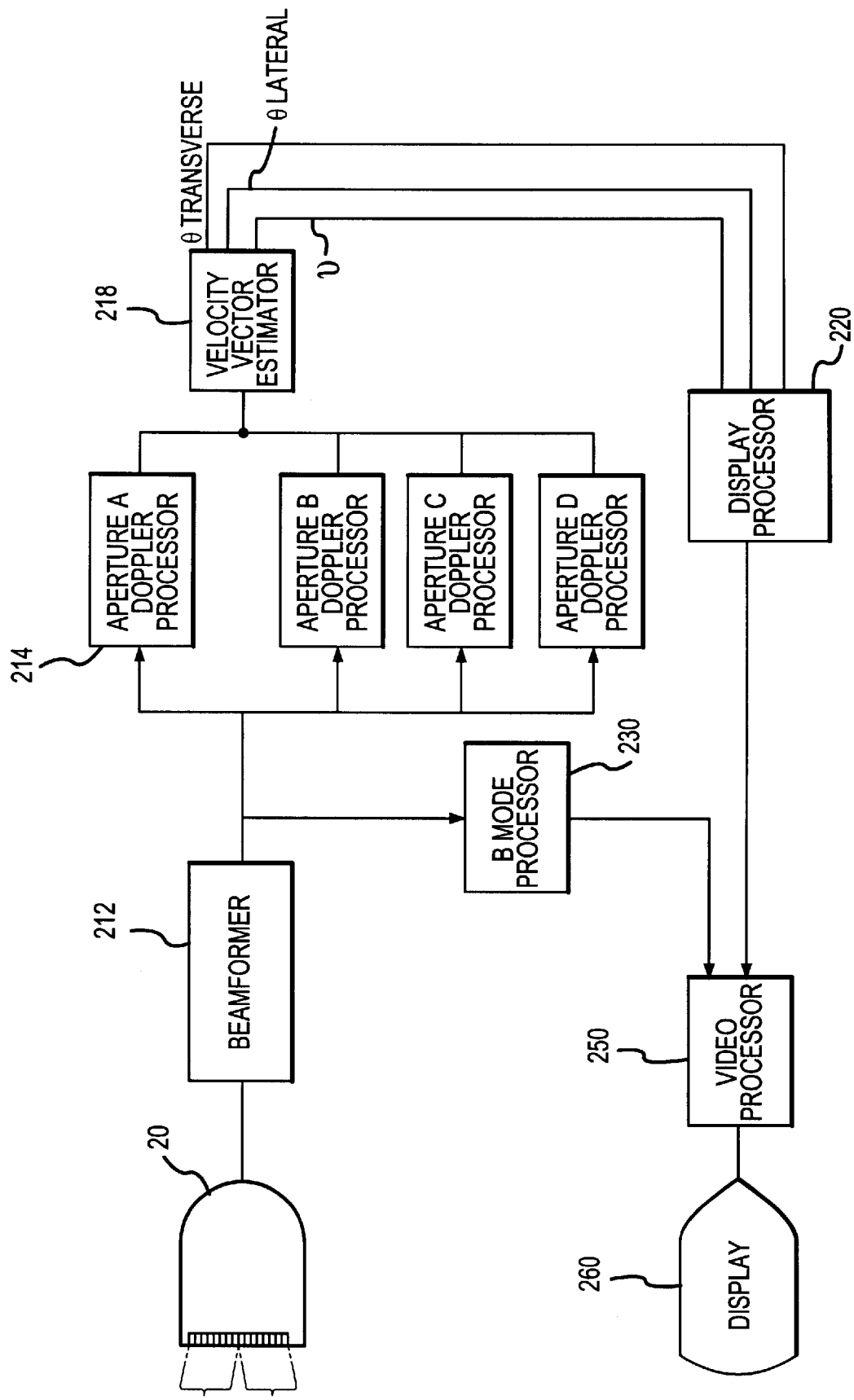
FIG. 6 is a block diagram of one embodiment of an ultrasound imaging unit used in the ultrasound imaging system of FIG. 1.

One embodiment of an imaging unit 30 (FIG. 1) that may be coupled to the scanhead 20 is shown in FIG. 6. The imaging unit 30 includes a beamformer 212 that effectively steers and focuses ultrasound beams received by the receive apertures 50–58 in the scanhead 20 to form scanlines of coherent echo signals. Output signals from the beamformer are applied to four Doppler processors 214a–d, which perform Doppler estimations of the Doppler phase shift or signal intensity (power Doppler) and generate signals indicative of the velocity, both direction and magnitude, of ultrasound returns received by the respective receive apertures 50, 52, 56, 58. More specifically, the first Doppler processor 214a determines velocity from ultrasound returns received by the receive aperture 50, the Doppler processor 214b determines velocity from ultrasound returns received by the receive aperture 52, the Doppler processor 214c determines velocity from ultrasound returns received by the receive aperture 56, and the Doppler processor 214d determines velocity from ultrasound returns received by the receive aperture 58. Conventionally this is done by Fourier transform or autocorrelation of Doppler signal data.

Based on the outputs from the Doppler processors 214, a velocity vector estimator 218 is able to determine the magnitude and direction of a composite Doppler motion vector in three dimensions. The velocity vector estimator produces a first signal V indicative of the magnitude of the flow vector, a second signal $\theta_{TRANSVERSE}$ indicative of the transverse angle, and a third signal $\theta_{LATERAL}$ indicative of the lateral angle. These signals are applied to a display processor 220, which converts the signals to an appropriate format for subsequent display. For example, the display processor 220 may format the signals so that magnitude of flow velocity or tissue motion is portrayed by color or intensity. The signals from the display processor 220 are applied to a video processor 250, which generates appropriate video signals, such as NTSC signals, for presentation on a suitable display 260, which may be a cathode ray tube.

The output signals from the beamformer 212 are also applied to a B Mode Processor 230, which processes amplitude information of the output signals from the beamformer 212 on a spatial basis. The B Mode Processor 230 generates signals that are applied to the Video Processor 250 to provide a structural image, preferably in three dimensions, of the tissue in the volume from which a Doppler image is being obtained. The structural image is preferably overlaid in the display 260 on the three-dimensional Doppler image.

Figure 7:
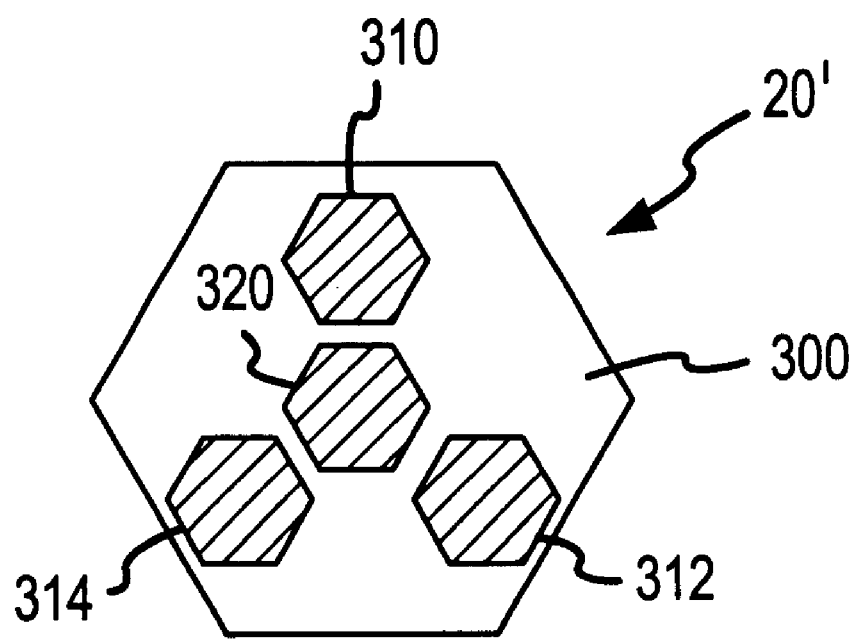
FIG. 7 is a plan view of a transducer face according to another embodiment of a scanhead that is may be used in the imaging system of FIG. 1.

A scanhead 20 having two pairs of receive apertures 50, 52 and 56, 58 arranged along axes 54, 60 that are perpendicular to each other is preferred for ease of processing the signals generated by the receive apertures. Specifically, the receive apertures 50, 52 and 56, 58 lying along the same axis 54 and 60, respectively, can be processed together to obtain a composite two-dimensional motion vector in respective planes that are perpendicular to each other, as previously explained. These two-dimensional vectors can then be combined to create a three-dimensional flow vector, as also previously explained. However, the invention may be practiced with any scanhead having three or more receive apertures arranged in a common plane. For example, as shown in FIG. 7, a scanhead 20' has a transducer face 300 containing three receive apertures 310, 312, 314. Located between the receive apertures 310–314 is a single transmitter aperture 320. The scanhead 20' has the advantage of using fewer receive apertures compared to the scanhead 20 of FIG. 2. However, it has the disadvantage of being computationally more difficult to combine the outputs from the receive apertures 310–314 because pairs of adjacent receive apertures 310–314 can determine a two-dimensional motion vector lying along each of three planes intersecting each other at 60 degrees.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An ultrasonic imaging system for generating a three-dimensional Doppler image, comprising:
   a scanhead comprising:
      at least three receive apertures each of which includes a plurality of transducer elements that steer and dynamically focus received signals; and
      a transmit aperture separate from and centrally located with respect to the receive apertures, the transmit aperture including a plurality of transducer elements that steer and focus transmitted signals; and
   an imaging unit comprising:
      a beamformer coupled to the receive apertures, the beamformer being structured to combine signals from at least three of the receive apertures to image an area adjacent the scanhead;
      a Doppler processor coupled to receive signals from the beamformer and being structured to generate a magnitude signal indicative of the Doppler motion magnitude of moving ultrasound reflectors in the imaged area and a direction signal indicative of the direction of the moving ultrasound reflectors in the imaged area;
      a velocity estimator coupled to receive the magnitude and direction signals from the Doppler processor, the velocity estimator operating on at least two combinations of signals, each from at least two receive apertures, and being structured to generate a magnitude signal indicative of the magnitude of a three dimensional motion vector corresponding to the magnitude signals from the Doppler processor and a motion angle signal indicative of the direction of the three dimensional motion vector corresponding to the direction signals from the Doppler processor;
      a display processor coupled to receive the three-dimensional magnitude signal and the three-dimensional motion angle signal from the velocity estimator, the display processor converting the three-dimensional magnitude and motion angle signals to a display signals having a predetermined display format; and
      a display coupled to receive the three-dimensional magnitude and motion angle signals from the display processor, the display providing a three-dimensional image of motion in a volume adjacent the scanhead.

2. The ultrasonic imaging system of claim 1 wherein the transmit aperture is positioned symmetrically between the receive apertures.

3. The ultrasonic imaging system of claim 1 wherein the imaging unit further comprises a B-mode processor coupled to receive a signal from the beamformer, the B-Mode processor being structured to generate signals that cause the display to generate a structural image.

4. The ultrasonic imaging system of claim 3 wherein the B-Mode processor is structured to generate signals that cause the display to generate a three-dimensional structural image.

5. The ultrasonic imaging system of claim 1 wherein the scanhead comprises:
   a first pair of receive apertures positioned in the common plane along a first axis; and
   a second pair of receive apertures positioned in the common plane along a second axis that is perpendicular to and intersects the first axis.

6. The ultrasonic imaging system of claim 5 wherein the transmit aperture is positioned in the common plane at the intersection of the first and second axes.

7. The ultrasonic imaging system of claim 1 wherein the plurality of receive apertures are equally spaced from a center point of the scanhead and circumferentially spaced from each other.

8. The ultrasonic imaging system of claim 7 wherein each of the receive apertures has a hexagonal shape.

9. The ultrasonic imaging system of claim 8 wherein the transmit aperture has a hexagonal shape.

10. The ultrasonic imaging system of claim 1 wherein the scanhead comprises a transducer face containing the receive and transmit apertures, the transducer face having a hexagonal configuration.

11. An ultrasound scanhead, comprising:
    a planar scanhead face;
    a first pair of receive apertures positioned in the scanhead face along a first axis, each of the receive apertures in the first pair including a plurality of transducer elements that steer and dynamically focus received signals;
    a second pair of receive apertures positioned in the scanhead face along a second axis that is perpendicular to and intersects the first axis, each of the receive apertures in the second pair including a plurality of transducer elements that steer and dynamically focus received signals; and
    a transmit aperture in the scanhead face separate face from and centrally located with respect to the receive apertures, the transmit aperture including a plurality of transducer elements that steer and focus transmitted signals.

12. The ultrasound scanhead of claim 11 wherein the transmit aperture is positioned in the scanhead face at the intersection of the first and second axes.

13. The ultrasound scanhead of claim 11 wherein the transducer face has a hexagonal configuration.

14. An ultrasound scanhead, comprising:
    a planar scanhead face;
    a plurality of receive apertures equally spaced from a center point of the scanhead face and circumferentially spaced from each other, each of the receive apertures including a plurality of transducer elements that steer and dynamically focus received signals; and
    a transmit aperture in the scanhead face separate from and centrally located with respect to the receive apertures, the transmit aperture including a plurality of transducer elements that steer and focus transmitted signals.

15. The ultrasound scanhead of claim 14 wherein each of the receive apertures has a hexagonal shape.

16. The ultrasound scanhead of claim 15 wherein the transmit aperture has a hexagonal shape.

17. The ultrasound scanhead of claim 14 wherein the scanhead face has a hexagonal configuration.

18. An ultrasonic imaging system for generating a three-dimensional Doppler image, comprising:
    a scanhead comprising:
       at least three receive apertures each of which includes a plurality of transducer elements that steer and dynamically focus received signals; and
       a transmit aperture separate from and centrally located with respect to the receive apertures, the transmit aperture including a plurality of transducer elements that steer and focus transmitted signals; and
       an imaging unit coupled to receive signals from the at least three receive apertures, the imaging unit being structured to generate a three-dimensional Doppler image based on the signals from the signals received from the receive apertures.

19. The ultrasonic imaging system of claim 18 wherein the transmit aperture is positioned symmetrically between the receive apertures.

20. The ultrasonic imaging system of claim 18 wherein the scanhead comprises:
 a first pair of receive apertures positioned in the common plane along a first axis; and
 a second pair of receive apertures positioned in the common plane along a second axis that is perpendicular to and intersects the first axis.

21. The ultrasonic imaging system of claim 20 wherein the transmit aperture is positioned in the common plane at the intersection of the first and second axes.

22. The ultrasonic imaging system of claim 18 wherein the plurality of receive apertures are equally spaced from a center point of the scanhead and circumferentially spaced from each other.

23. The ultrasonic imaging system of claim 22 wherein each of the receive apertures has a hexagonal shape.

24. The ultrasonic imaging system of claim 23 wherein the transmit aperture has a hexagonal shape.

25. The ultrasonic imaging system of claim 18 wherein the scanhead comprises a transducer face containing the receive and transmit apertures, the transducer face having a hexagonal configuration.

26. A method of displaying a three-dimensional Doppler image, comprising:
 directing at least one beam of transmitted ultrasound energy into tissues or vessels to be imaged, the beam of transmitted ultrasound energy being steered and focused within the tissues or vessels;
 receiving at least three beams of ultrasound reflections from the tissues or vessels, each of the beams of ultrasound reflections being received at respective non-colinear locations in a common plane symmetrically arranged around and spaced from the beam of transmitted ultrasound energy, each of the beam of ultrasound reflections being steered and dynamically focused within the tissues or vessels; and
 processing the beams of ultrasound reflections to generate a three-dimensional Doppler image.

27. The method of claim 26 wherein the act of processing the beams of ultrasound reflections further comprises processing the beams of ultrasound reflections to generate a structural image.

28. The method of claim 27 wherein the act of processing the beams of ultrasound reflections further comprises overlaying the structural image on the three-dimensional Doppler image.

29. The method of claim 26 wherein the act of processing the beams of ultrasound reflections to generate a structural image comprises processing the beams of ultrasound reflections to generate a three-dimensional structural image.

30. The method of claim 29 wherein the act of processing the beams of ultrasound reflections further comprises overlaying the three-dimensional structural image on the three-dimensional Doppler image.

\* \* \* \* \*